United States Patent [19]

Meadow et al.

[11] Patent Number: 5,262,018
[45] Date of Patent: Nov. 16, 1993

[54] METALS REMOVAL FROM AQUEOUS PEROXY ACIDS OR PEROXY SALTS

[75] Inventors: Morton Meadow, Trenton, N.J.; Charles J. Lymburner, Williamsville, N.Y.; C. Andrew Thompson, Newtown, Pa.

[73] Assignee: FMC Corporation, Philadelphia, Pa.

[21] Appl. No.: 743,953

[22] Filed: Aug. 12, 1991

[51] Int. Cl.$^5$ .............................................. C25B 1/28
[52] U.S. Cl. ...................................... 204/82; 204/93; 210/638
[58] Field of Search .................... 204/82, 93; 210/638

[56] References Cited

U.S. PATENT DOCUMENTS

| | | | |
|---|---|---|---|
| 3,616,325 | 10/1971 | Mucenieks | 204/82 |
| 4,144,144 | 3/1979 | Radimer et al. | 204/82 |
| 4,310,394 | 1/1982 | Malafosse et al. | 204/82 |
| 4,591,443 | 5/1986 | Brown et al. | 210/747 |
| 4,610,795 | 9/1986 | Norris et al. | 252/8.551 |
| 4,626,327 | 12/1986 | McCarthy et al. | 204/82 |
| 4,663,002 | 5/1987 | Chiang et al. | 204/82 |

OTHER PUBLICATIONS

Sengupta et al., Metal(II) Ion Binding onto Chelating Exchangers with Nitrogen Donor Atoms: Some New Observations and Related Implications, Environ. Sci. Technol., vol. 25:481-88 (1991).
Chem. Abstracts, III, 198,978b (1989), The Cobrex Process, Himsley et al.

*Primary Examiner*—John Niebling
*Assistant Examiner*—Brian M. Bolam
*Attorney, Agent, or Firm*—R. E. Elden; P. C. Baker; R. L. Andersen

[57] ABSTRACT

A process for purifying a peroxygen compound in an aqueous solution of a peroxygen-stable acid or salt of the acid, comprising contacting the aqueous solution at a pH of about 0.5 to 4 with a chelating ion exchange resin and separating the product as a purified aqueous solution, or optionally as a solid.

11 Claims, No Drawings

METALS REMOVAL FROM AQUEOUS PEROXY ACIDS OR PEROXY SALTS

The present invention is a process for purifying an aqueous solution of a peroxy acid or peroxy salt.

Transition metals are known to be catalysts for peroxygens, either as free radical initiators, as disclosed in U.S. Pat. No. 4,591,443, or as decomposition catalysts and hence, are generally not desired therein. Transition metals are also objectionable in solutions used to treat semiconductors and the like. Therefore, it is very important to avoid the presence of transition metals in solutions of peroxygens, particularly in aqueous solutions of peroxy salts of acids, such as potassium peroxydiphosphate, potassium peroxymonosulfate, and potassium, sodium or ammonium peroxydisulfate (persulfate).

It is difficult to avoid accumulating transition metals during the production of peroxy compounds of sulfuric, phosphoric and acetic acid, particularly the transition metals iron, nickel, cobalt, copper, molybdenum, and the like used in constructing production equipment in a plant, particularly when part of the solution is recycled as in U.S. Pat. Nos. 4,663,002 and 4,144,144. In these processes part of the process liquor is recycled during electrolysis.

For example, solutions of sodium persulfate and ammonium persulfate produced by electrolytic methods often contain small amounts of metallic impurities, primarily iron. These impurities were previously either removed by raising the pH of the electrolytic solutions from about 1.0 to about 7.2 to 7.5 in order to precipitate iron in the form of a gelatinous iron hydroxide, or, alternatively, precipitated as an iron cyanide complex salt, such as, Prussian Blue (ferric ferrocyanide). Purification by neutralization is unsatisfactory because substantial amounts of ammonia (for ammonium persulfate solutions) or sodium hydroxide (for sodium persulfate solutions) are required in order to raise the pH of these solutions. Furthermore, complete neutralization can cause control problems and can upset the process balance. Purification by precipitation of an iron cyanide complex is unsatisfactory because any peroxygen must be destroyed before precipitating the gelatinous iron cyanide complex.

The gelatinous iron hydroxide precipitate or iron cyanide complex are both difficult to remove by ordinary filtration; the mixture is usually filtered through diatomaceous earth coated filters. At times, some of the diatomaceous earth escapes filtration and contaminates the persulfate-containing filtrate with an insoluble material. When the coated filters become loaded with iron hydroxide or iron cyanide complex, the contaminated coating must be removed and disposed of, always in landfills.

The present invention overcomes the problems of the prior art by providing a process for reducing the concentration of ions of transition metals in aqueous solutions of peroxy acids or their salts, comprising contacting the aqueous solution at a pH of about 0.5 to about 4 with a sufficient quantity of a chelating ion exchange resin in the acid form to remove at least part of the transition metal ions from the aqueous solution, and separating as product a purified aqueous solution containing a substantially reduced concentration of transition metal ions.

More specifically, the invention is a process for reducing the concentration of ions of transition metals in aqueous solutions of a peroxydiphosphate, peroxydisulfate or of peroxymonosulfate, comprising contacting the aqueous solution at a pH of about 0.5 to about 4 with a sufficient quantity of a chelating ion exchange resin in the acid form to remove at least part of the transition metal ions from the aqueous solution, and separating as product a purified aqueous solution containing a substantially reduced concentration of transition metal ions.

The scope of the present invention is intended to include a process for anodically oxidizing an aqueous electrolytic solution of an alkali metal or ammonium sulfate or phosphate to the corresponding peroxydisulfate or peroxydiphosphate by reducing or decreasing the concentration of ions of transition metals in the aqueous electrolytic solution by contacting the aqueous electrolytic solution at a pH of about 0.5 to about 4 with a sufficient quantity of a chelating ion exchange resin in the acid form to remove at least part of the transition metal ions from the aqueous electrolytic solution, and separating as product a purified aqueous electrolytic solution containing a substantially reduced concentration of transition metal ions and optionally recovering the solid product.

Peroxy acids are also commonly called peroxyacids or peracids. Sulfuric acid, phosphoric acid, acetic acid and formic acid all form peroxyacids or salts. Typical salts of peroxyacids are the water-soluble stable alkali metal and ammonium salts of peroxydisulfate acid, peroxymonosulfuric acid, peroxydiphosphoric acid, and the triple salt potassium monopersulfate-potassium sulfate-potassium bisulfate. Typical peracids are performic acid, peracetic acid and monopersulfuric acid (Caro's acid). Unless otherwise obvious the term "persulfate" refers to peroxydisulfate.

The process of this invention is particularly useful for removing transition metal impurities from either ammonium persulfate or sodium persulfate electrolytic solutions by contacting these solutions with a chelating ion exchange resin. The process may be conducted in a batch or a continuous mode and usually requires only a minor pH adjustment of the electrolytic solution. The process is also useful for removing transition metals from aqueous solutions being employed in applications such as etching metals and the like. The process is described in detail in terms of a persulfate for clarity.

It has been discovered that by adjusting the pH of persulfate solutions containing metallic impurities to about 0.5 to 4 and preferably to about 2.0 to 4.0, the impurities may be completely, or nearly completely, removed by employing a chelating cation exchange resin such as Amberlite® IRC-718 chelatin resin or Duolite® C-467 chelating resin, preferably in the hydrogen ion or acidic form. Metallic impurities such as iron, nickel, chromium, manganese, cobalt, and copper can be removed, or reduced to very low levels.

Transition metals are the metals designated by the International Union of Pure and Applied Chemistry as groups IB, IIB, IIIA, IVA, VA, VIA, VIIA and VIIIA of rows 4 to 7 of the periodic table (e.g. atomic Nos. 21 to 30 etc.). One skilled in the art will recognize that the aqueous solutions may optionally contain other compounds such as fluorides, thiocyanates, and free radical traps such as phenols, allyl alcohols and the like. The aqueous solutions may alternatively contain a free radical initiator and other compounds frequently employed during the manufacture or use of a peroxygen compound.

The electrolytic processes currently used for the preparation of ammonium persulfate and sodium persulfate produce persulfate liquors which, when they contain metallic impurities, have a color ranging from pink to yellow or to brown, depending on the amount of iron that is present. It is preferred that metallic impurities be absent since, during crystallization, the impurities can be trapped in the crystalline product, making it inferior to product containing little or none of these impurities. The process of the present invention requires only a small change in the pH of the liquor, to the range of about 0.5 to about 4, in order for the chelating resins to remove the impurities. Not only does this avoid the control problems and the potential upset of the process balance which may result from more complete neutralization, but it also results in a considerable savings in the amount and total cost of alkaline material used when compared to current processes which raise the pH above 7.0.

Chelating ion exchange resins (chelating resins) differ from the well-known salt forming ion exchange resins, such as sulfonic acid ion exchange resins which have sulfonic acid functionalities. Instead, chelating ion exchange resins may have iminodiacetic acid functional groups (marketed under the trademarks or designation Amberlite IRC-718 and Chelex 20), amino-phosphonic acid functional groups (marketed under the tradename Duolite C-467), or may be a N-hydroxypropylpicolylamine functionalized chloromethylated polymer (marketed under the tradenames Dowex XFS-4195 and Dowex XFS-43084), and the like. The chelating ion exchange resins with iminodiacetic functionalities and amino-phosphonic acid functionalities are preferred for removing iron ions from solutions of ammonium and sodium sulfate containing a persulfate. However, one skilled in the art will be able to select the optimum chelating ion exchange resin for removing other transition metals from any particular solution without undue experimentation.

The use of a chelating ion exchange resin eliminates the need and capital and operating cost of diatomaceous earth coated filters and subsequent disposal of the spent filter medium. In addition, the chelating cation exchange resins are easily regenerated with sulfuric acid and may be regenerated many times without losing the ability to remove metallic impurities. Sulfuric acid, the preferred regenerant, is used in the electrolytic processes for both ammonium and sodium persulfate and is thus system compatible.

Eight commercially-available sulfonic acid ion exchange resins and five chelating resins have been evaluated for their efficacy in removing iron from a solution containing by weight, water 59.0%, sodium persulfate 22.0%, ammonium sulfate 9.5%, and sodium sulfate 9.5%.

Ferric ammonium sulfate was added to this mixture to provide a concentration of about 20 mg/l of iron ("Test Solution"). The concentrations of iron and other metallic impurities were measured by either of two spectroscopic methods. The older, but more sensitive, method is graphite furnace atomic absorption spectroscopy which is capable of measuring one element at a time. The newer method is inductively coupled plasma atomic emission spectroscopy which is capable of multielement measurements simultaneously.

It is known that the selectivity of ordinary ion exchange resins for metal ions depends on many factors, one of them being the pH of the solution. Therefore, the commercially-available ion exchange resins were tested in a range of pH from about 0.5 to about 4. It was determined from these tests that the sulfonic acid ion exchange resins were ineffective within these pH limits. Unexpectedly, even the chelating resins, normally supplied and used in a sodium salt form, were not effective until converted to the acidic form by treatment with sulfuric acid. Two of these resins, designated Amberlite IRC-718 and Duolite C-467, were effective in significantly reducing the iron content in the pH range tested. A third resin, designated Chelex 20, reduced the iron content of the persulfate solution somewhat in the pH range of 2 to 4.

Although the present invention is not dependent upon any theory of operation or mechanism, it is convenient to explain the ineffectiveness of the chelating ion exchange resins when employed in their normally-used sodium form as a result of precipitation.

The chelating resins are normally supplied and used in the sodium salt form. Attempts to use this commercially-available form of Amberlite IRC-718, Duolite C-467, and Chelex 20 chelating resins unexpectedly caused iron to precipitate when the resin was mixed with the persulfate solution. Thus, these resins in the sodium form failed to remove the iron by forming a stable complex with the resin.

An important and unexpected advantage of using the acidic form of chelating resin instead of the usual sodium form is that the regeneration process is simpler and is less costly. Regeneration of the sodium form of a chelating resin requires 1) converting the spent resin to the acidic form using a mineral acid, and 2) treating the acidic resin with a hydroxide of the desired cation, e.g., sodium hydroxide. Using the process of the present invention, the acidic chelating resin may be regenerated by simply washing the spent resin with a mineral acid, preferably sulfuric acid, which does not add any foreign component to a persulfate solution and provides in a single step both an initial activation and a subsequent regeneration process. It is expected that the acidic chelating resin of the current invention may be regenerated and reused many times. This promises a considerable savings in cost and more important, a reduction in the volume of waste which requires disposal, especially after filtering through diatomaceous earth or other filter aid.

The process is operable over a wide pH range of about 0.5 to about 4.0. At a pH greater than 4.0 the transition metals, such as iron, tend to precipitate as the hydroxide. For the removal of low concentrations of metallic impurities, such as iron, from sodium persulfate mixtures, the Duolite C-467 chelating resin was found to be efficient over the pH range of 0.5 to 4, preferably between a pH of 1 to 3. Amberlite IRC-718 and Chelex 20 chelating resins are efficient in the pH range of 2 to 4, preferably between a pH of 3 and 4. Aqueous sodium hydroxide is preferred for a pH adjustment of the sodium persulfate solution.

For the purification of ammonium persulfate mixtures, Amberlite IRC-718 and Duolite C-467 chelating resins work well within a pH range of 1 to 4 and are most efficient at a pH of about 2 to 3. Adjustment of pH of the ammonium persulfate solutions may be done by adding ammonia gas to the solution, or by adding aqueous ammonium hydroxide.

The present process is applicable to both a batch mode and a continuous method of operation. In the batch mode of operation the persulfate solution can be stirred with the resin for a period of time during which the metal impurities are removed or reduced to acceptable levels. The length of time is dependent on the amount of impurities present in the persulfate solution, the amount of resin used, the capacity of the resin, and the pH of the solution. For persulfate solutions containing between 10 and 20 mg/l of iron, it is suggested that the presently-available chelating exchange resins be used in a range of 5% to 20% by volume, preferably about 10%. For example, to treat 100 ml of persulfate at the preferred pH, approximately 10 ml of the chelating exchange resin should be used. The time required for this process is usually 20 minutes to one hour. Of course, other conditions may be selected for particular applications.

For the continuous mode of operation, the resin is contained in a column and the persulfate solution is flowed through the resin bed. For the presently available chelating resins the rate at which the persulfate solution is flowed through the resin bed may be in the range of one to three times the volume of the resin used per hour, preferably two times. In laboratory tests it was found that a flow rate of twice the volume of the resin bed per hour worked best, e.g., if 10 ml of resin was used, a rate of 20 ml per hour reduced the iron content of the persulfate solution to less than 1 mg/l. The continuous mode of operation is more efficacious and is therefore the preferred method. Upward flow through the bed is also preferred over downward flow because it frees the bed of any gassing and avoids channeling. Occurrence of either of these effects would greatly reduce the effectiveness of the treatment to remove metallic impurities.

Any temperature above 0° C. may be employed at which the aqueous solution is a liquid. The maximum temperature is limited by the acceptable decomposition rate. Practically any temperature up to about 60° C. generally may be employed. For the most efficient operation of this process it is desirable that the persulfate solution be in a temperature range of about 25° C. to about 45° C., preferably in the range of about 30° C. to 40° C. The persulfate solutions prepared by electrolytic processes are very concentrated and may even be at the point of saturation. If the temperature of these solutions is allowed to fall too low, crystallization problems complicate the process. Water may be added to dilute the solution, thus preventing crystallization problems; however, this water must be removed later in order to recover the ammonium or sodium persulfate, thus adding extra expense to the process. It is therefore preferred to operate at an elevated temperature to prevent crystallization rather than diluting the solution with water.

The following examples are intended to illustrate the invention but not to narrow the scope thereof.

Unless otherwise specified, all percentages are by weight. Although this invention is exemplified in terms of sodium and ammonium persulfate, one skilled in the art will recognize that any soluble salt of a peroxygen-stable acid, such as, a phosphate, acetate, nitrate may be employed provided the cation is not a transition metal. Suitable salts include ammonium phosphate, ammonium sulfate, ammonium acetate, alkali metal phosphates, sulfates and acetates, and the like. The resin designations are available from manufacturers as follows: Rohm and Haas, "Amberlite" and "Amberlyst," Dow, "Dowex;" Ionac, "Diaion" and "Ionac;" and BioRad, "Chelex".

EXAMPLE 1

A 50 ml portion of Amberlite IRC-718 chelating resin, sodium form, was washed with 250 ml of an aqueous, 15% sulfuric acid solution. The washed resin was thoroughly rinsed with deionized water, leaving the resin in the acid form. Two four liter samples of electrolytic sodium persulfate anolyte were produced by the process described in Examples 6, 7, and 8 of U.S. Pat. No. 4,144,144. The samples were analyzed for pH and metallic impurities. Table I shows the amounts of metallic impurities determined to be in these two samples. The first solution, which was pink in color, had a pH of 1.17. The second solution, which had a yellow color, had a pH of 4.3. One skilled in the art will recognize that such a solution will also contain monopersulfates and hydrogen peroxide.

A 20 ml portion of the first sodium persulfate solution (pH 1.17) was gravity fed through a bed (10 ml) of the acidic IRC-718 chelating resin. The color of the eluate was a very light yellow. Likewise, a 20 ml portion of the second sodium persulfate solution (pH 4.3) was gravity fed through a bed (10 ml) of the acidic IRC-718 chelating resin. This eluate had a faint yellow color. Each of the eluates was analyzed for metallic impurities; the results of these analyses are summarized in Table I.

By feeding the electrolytically produced sodium persulfate solution through the acidic form of Amberlite IRC-718 chelating resin, the metallic impurities present were dramatically reduced. The iron content of these solutions was reduced by 16% and 96%, respectively, for the first and second solutions. This example also shows that the process is not specific to persulfate (peroxydisulfate), but is operable in the presence of any of the peroxygen compounds found in the electrolyte (hydrogen peroxide, peroxymonosulfate and peroxydisulfate).

EXAMPLE 2

A 70 ml sample of Amberlite IRC-718 chelating exchange resin, sodium form, was converted to the acid form by washing with two successive 70 ml portions of aqueous, 15% sulfuric acid solutions. The resin was washed in succession with an additional 70 ml of 15% sulfuric acid and 1.5 l of deionized water, leaving the IRC-718 chelating resin in its acidic form. A sodium persulfate Test Solution was prepared as described earlier.

The Test Solution was divided into five 20 ml portions. The pH of each portion was adjusted using sodium hydroxide to provide a pH range of 0.51 to 4.00. Ten milliliters of the acidified IRC-718 chelating resin was added to each sodium persulfate solution, and the mixtures were stirred for 30 minutes. Each mixture was filtered, and the filtrates were analyzed for iron concentration. The results of this experiment are summarized in Table II.

It is clear that when the pH of the sodium persulfate solution is 3 or less, more than 50% of the iron dissolved in the solution may be removed by the acidic form of Amberlite IRC-718 chelating resin.

EXAMPLE 3

In a manner similar to Example 2, 70 ml of Amberlite IRC-718 and 70 ml of Duolite C-467 chelating resins were converted to their acidic form. A solution was prepared containing by weight 54.4% water, 19.3% ammonium sulfate and 26.3% ammonium persulfate. Ferric ammonium sulfate was added to provide an iron concentration of 7.4 mg/l. This mixture was divided into eight 20 ml portions, and the pH of each portion was adjusted with ammonium hydroxide to provide two sets of solutions, each with a pH range of about 1 to about 4; i.e., two portions with a pH of about 1; two portions with a pH of about 2, two portions with a pH of about 3, and two portions with a pH of about 4.

Ten milliliters of acidified IRC-718 chelating resin was added to one of each pair of solutions, and 10 ml of the acidified C-467 chelating resin was added to the other one of each pair of solutions. Each mixture was stirred for 30 minutes and was filtered. The filtrates were analyzed for iron content. These results are summarized in Table III.

More than 50% of the iron content of the ammonium persulfate solution was removed by treating the solution with the acidic form of Amberlite IRC-718 chelating resin at a pH of between 3 and 4. The acidic form of Duolite C-467 chelating resin removed over 50% of the dissolved iron at each pH tested, being most effective in the pH range of 2 to 3.

EXAMPLE 4

The acidic form of Duolite C-467 chelating resin (60 ml) was prepared by the method of Example 2, and 30 ml of this resin was placed in an 18"×½" glass column fitted with a 110 mesh Teflon ® brand screen at the top and bottom. A sodium persulfate solution was pumped through the acidic C-467 chelating resin bed at a rate of about 50 ml per hour, the solution contained 2334 g water, 247 g ammonium sulfate, 247 g sodium sulfate, and 572 g sodium persulfate.

The following metal salts were added to provide the concentration of metal impurities indicated in parentheses: ferric ammonium sulfate dodecahydrate (47 mg/l iron); nickel sulfate hexahydrate (6.6 mg/l nickel); and chromium potassium sulfate dodecahydrate (5.9 mg/l chromium). The pH of this solution was adjusted to 3.0 using sodium hydroxide. Additional sodium persulfate solution was prepared as needed. The eluate, the column effluent, was analyzed for metal content; the results of these analyses are summarized in Table IV. On the fifth day (~120 hours after beginning this experiment) the resin was washed with 250 ml of sulfuric acid. This wash was analyzed for metallic impurities with the following results: iron=1900 mg/l; nickel=13 mg/l; and chromium=11 mg/l. A second wash of the resin with 250 ml of hydrochloric acid was made. Analysis of this wash for metallic impurities was: iron=19 mg/l; nickel=12 mg/l; and chromium=7.1 mg/l.

EXAMPLE 5

A number of ion exchange resins were evaluated for their efficacy in removing iron from sodium persulfate solutions by the method of Example 2. The data and results are presented as Table V. A similar evaluation of chelating resins is presented as Table VI. This very simple screening method may be used to determine the efficacy of a chelating resin to remove any specific transition metal from any particular peroxygen solution (here removing iron from sodium persulfate solutions).

TABLE I

REMOVAL OF METALS FROM PERSULFATE ANOLYTE

| Sample | Metallic Impurity Analysis (mg/l) | | | | | |
|---|---|---|---|---|---|---|
| | Fe | Ni | Cr | Mn | Co | Cu |
| First Solution Feed | 50 | 11 | 16 | 2.1 | 0.12 | 1.4 |
| First Eluate | 37 | 10 | 13 | 2.2 | 0.13 | 1.3 |
| Second Solution | 35 | 7.8 | 11 | 0.79 | 0.08 | 0.94 |
| Second Eluate | 1.4 | 4.8 | 3.6 | 1.2 | 0.07 | <0.1 |

TABLE II

EFFECT OF pH ON IRON REMOVAL WITH IRC-718 CHELATING RESIN FROM SODIUM PERSULFATE

| pH of Solution | Iron Content (mg/l) | % Iron Reduction |
|---|---|---|
| 4.00 | 9.5 | 52.5 |
| 2.95 | 10.0 | 50.0 |
| 1.93 | 12.0 | 40.0 |
| 1.02 | 18.0 | 10.0 |
| 0.51 | 19.0 | 5.0 |

TABLE III

EFFECT OF pH ON IRON REMOVAL FROM AMMONIUM PERSULFATE SOLUTIONS

| Acidic Resin | pH | Iron Content mg/l | % Iron Reduction |
|---|---|---|---|
| Amberlite IRC-718 | 3.94 | 3.5 | 52.7 |
| Amberlite IRC-718 | 2.93 | 2.3 | 68.9 |
| Amberlite IRC-718 | 2.01 | 3.9 | 47.3 |
| Amberlite IRC-718 | 1.00 | 6.3 | 14.9 |
| Duolite C-467 | 3.90 | 3.1 | 58.1 |
| Duolite C-467 | 2.94 | 1.3 | 82.4 |
| Duolite C-467 | 2.01 | 1.8 | 75.7 |
| Duolite C-467 | 1.01 | 2.6 | 64.9 |

TABLE IV

TRANSITION METALS REMOVAL BY CHELATING RESIN

| Time (Hr.) | Volume Through Column (ml) | mg/l | | |
|---|---|---|---|---|
| | | Iron | Nickel | Chromium |
| 0 | Initial analysis | 47 | 6.6 | 5.9 |
| 6 | 460 | <1 | <1 | 3.9 |
| 23 | 1870 | <1 | 3.6 | 2.0 |
| 30 | 2440 | <1 | 5.6 | 4.1 |
| 47 | 3870 | <1 | 7.2 | 3.5 |
| 54 | 4440 | <1 | 6.8 | 4.1 |
| 72 | 5800 | 2.3 | 7.8 | 4.2 |
| 96 | 6540 | 9.7 | 7.1 | 6.5 |

TABLE V

TREATMENT OF SODIUM PERSULFATE SOLUTIONS WITH THE ACIDIC FORM OF ION EXCHANGE RESINS TO REDUCE IRON CONTENT

| Resin (in Acidic Form) | pH of Persulfate Solution | Iron Content of Persulfate Solution Before/After Treatment (mg/l) |
|---|---|---|
| Amberlyst 15 | 4.00 | 21/21 |
| | 2.96 | 21/21 |
| | 2.05 | 21/21 |
| Amberlyst 200 | 4.05 | 21/21 |
| | 2.94 | 21/21 |
| | 2.03 | 21/20 |
| Amberlyst XN-1010 | 4.10 | 21/20 |
| | 2.96 | 21/21 |
| | 2.01 | 21/20 |
| Diaion HPK25 | 4.00 | 20/20 |
| | 3.04 | 20/20 |
| | 2.02 | 20/20 |
| Diaion PK228 | 4.10 | 20/20 |
| | 2.95 | 20/20 |

TABLE V-continued
TREATMENT OF SODIUM PERSULFATE SOLUTIONS WITH THE ACIDIC FORM OF ION EXCHANGE RESINS TO REDUCE IRON CONTENT

| Resin (in Acidic Form) | pH of Persulfate Solution | Iron Content of Persulfate Solution Before/After Treatment (mg/l) |
| --- | --- | --- |
| Dowex MSC-1-H | 1.98 | 20/20 |
|  | 4.04 | 20/20 |
|  | 2.97 | 20/20 |
| Dowex M-33 | 2.01 | 20/20 |
|  | 4.03 | 20/20 |
|  | 3.00 | 20/20 |
| Ionac CFP110 | 1.98 | 20/20 |
|  | 4.05 | 20/20 |
|  | 3.01 | 20/20 |
|  | 2.01 | 20/20 |

TABLE VI
TREATMENT OF SODIUM PERSULFATE SOLUTIONS WITH THE ACIDIC FORM OF ADDITIONAL CHELATING RESINS TO REDUCE IRON CONTENT USING THE BATCH METHOD OF EXAMPLE 2

| Resin (in acidic form) | pH of Solution | Iron Content Before/After Treatment (mg/l) |
| --- | --- | --- |
| Chelex 20 | 4.02 | 20/13 |
|  | 3.00 | 20/11 |
|  | 2.00 | 20/14 |
|  | 1.01 | 20/20 |
|  | 0.61 | 20/20 |
| Duolite C467 | 4.07 | 20/13 |
|  | 2.94 | 20/11 |
|  | 2.05 | 20/8.4 |
|  | 1.01 | 20/10 |
| Dowex XFS-4195 | 3.98 | 22/22 |
|  | 3.01 | 22/22 |
|  | 2.04 | 22/22 |
|  | 1.00 | 22/17 |
| Dowex XFS-43084 | 3.96 | 22/22 |
|  | 2.94 | 22/22 |
|  | 2.00 | 22/22 |
|  | 1.01 | 22/22 |

What is claimed is:

1. A process for reducing the concentration of ions of transition metals in aqueous solutions of peroxy acids or salts, comprising contacting the aqueous solution from about pH 0.5 to about pH 4 with a sufficient quantity of a chelating ion exchange resin in the acid form to remove at least part of the transition metal ions from the aqueous solution, and separating as product a purified aqueous solution containing a substantially reduced concentration of transition metal ions.

2. The process of claim 1 wherein the peroxy acids or salts are selected from the group consisting of permonosulfuric acid, perdisulfuric acid, perphosphoric acid, performic acid, peracetic acid, and alkali metal and ammonium salts thereof.

3. The process of claim 1 wherein the chelating ion exchange resin has a functional group selected from iminoacetic acids, amino-phosphonic acids and N-hydroxypicolylamines.

4. The process of claim 2 wherein the chelating ion exchange resin has a functional group selected from iminoacetic acids, amino-phosphonic acids and N-hydroxypicolylamines.

5. A process for reducing the concentration of ions of transition metals in aqueous solutions of a peroxygen compound and an alkali metal persulfate or ammonium persulfate, comprising contacting the aqueous solution from about pH 0.5 to about pH 4 with a sufficient quantity of a chelating ion exchange resin in the acid form to remove at least part of the transition metal ions from the aqueous solution, and separating as product a purified aqueous solution containing a substantially reduced concentration of transition metal ions.

6. The process of claim 5 wherein the chelating ion exchange resin has a functional group selected from iminoacetic acids, amino-phosphonic acids and N-hydroxypicolylamines.

7. In a process for anodically oxidizing an aqueous electrolytic solution of an alkali metal or ammonium sulfate or phosphate to the corresponding peroxydiphosphate or peroxydisulfate, the improvement comprising reducing the concentration of ions of transition metals in the aqueous electrolytic solution by contacting the aqueous electrolytic solution at a pH of about 0.5 to about 4 with a sufficient quantity of a chelating ion exchange resin in the acid form to remove at least part of the transition metal ions from the aqueous electrolytic solution, and separating as product a purified aqueous electrolytic solution containing a substantially reduced concentration of transition metal ions.

8. The process of claim 7 wherein the aqueous electrolytic solution comprises aqueous ammonium sulfate.

9. The process of claim 7 wherein the aqueous electrolytic solution comprises aqueous sodium sulfate.

10. The process of claim 7 wherein the aqueous electrolytic solution comprises aqueous potassium sulfate.

11. The process of claim 7 wherein the aqueous electrolytic solution comprises aqueous potassium phosphate.

* * * * *